US006187298B1

(12) United States Patent
Kurz et al.

(10) Patent No.: US 6,187,298 B1
(45) Date of Patent: Feb. 13, 2001

(54) SUNSCREENS HAVING ULTRASPECTRAL PROTECTION

(75) Inventors: Thekla Kurz; Sabine Hitzel; Dorothee Wille, all of Darmstadt (DE)

(73) Assignee: Merck Patent Gesellschaft mit beschrankter Haftung (DE)

( * ) Notice: Under 35 U.S.C. 154(b), the term of this patent shall be extended for 0 days.

(21) Appl. No.: 09/562,961

(22) Filed: May 3, 2000

Related U.S. Application Data

(63) Continuation of application No. 09/131,692, filed on Aug. 10, 1998, now abandoned.

(30) Foreign Application Priority Data

| Aug. 9, 1997 | (DE) | 197 34 582 |
| Oct. 18, 1997 | (DE) | 197 46 139 |
| Nov. 12, 1997 | (DE) | 197 50 028 |
| Jul. 8, 1998 | (DE) | 198 30 531 |

(51) Int. Cl.[7] ............... A61K 7/42; A61K 7/44; A61K 7/00; C09C 1/36
(52) U.S. Cl. ............... 424/59; 424/60; 424/400; 424/401; 106/436

(58) Field of Search ............... 424/59, 60, 400, 424/401; 106/436

(56) References Cited

U.S. PATENT DOCUMENTS

| 4,038,099 | 7/1977 | DeLuca, Jr. et al. . |
| 4,820,501 | 4/1989 | Wortzman . |
| 4,828,825 | 5/1989 | Weber et al. . |
| 5,593,680 | 1/1997 | Bara et al. . |

OTHER PUBLICATIONS

"Concise Encyclopedia of Chemistry", Berlin, NY: de Gruyter, p. 250.

*Primary Examiner*—Shelley A. Dodson
(74) *Attorney, Agent, or Firm*—Millen, White, Zelano & Branigan, P.C.

(57) ABSTRACT

The invention relates to novel light protection filters for the VIS and IR region for the preparation of sunscreens and also to the use thereof in cosmetics. The invention further relates to sunscreens which have broad-band or ultraspectral protection.

22 Claims, No Drawings

SUNSCREENS HAVING ULTRASPECTRAL PROTECTION

This is a continuation of application Ser. No. 09/131,692 filed Aug. 10, 1998, now abandoned.

The present invention relates to a cosmetic preparation which has ultraspectral protection or else broad-band protection against solar radiation. The invention also relates to novel light protection filters for the preparation of sunscreens and to the use in cosmetics.

While about 30 years ago sunlight was regarded as healing and safe because of its ability to synthesize vitamin D, in recent years the attitude in this respect has changed considerably, not only for medical reasons. There is increasing awareness of the potential dangers which are associated both with natural and also artificial solar irradiation. In particular, there has even been a change in behavior as a result of knowledge about the influence of sunlight on skin aging and the formation of skin cancer.

As is known, the skin is sensitive to solar rays, which may cause common sunburn or an erythema, but also burns of varying severity.

Solar rays do, however, also have other negative effects: they cause the skin to lose its elasticity and develop wrinkles and thus lead to premature aging. Dermatoses are also sometimes observed, and in extreme cases, skin cancer may result.

On the basis of this knowledge, there have been some developments in sun protection. While up to just a few years ago, the principal aim was an erythema-inhibiting UVB protection, protection against UVA radiation is now included in sunscreen formulations. UVA radiation is essentially a trigger for pigmenting the skin.

It is also desirable to protect hair against photochemical damage in order to avoid changes in shades, bleaching or damage of a mechanical nature.

As is known, the most dangerous part of solar rays comprises the ultraviolet rays having a wavelength of less than 400 nm. It is also known that as a result of the presence of the ozone layer in the Earth's atmosphere, which absorbs some solar radiation, the lower limit of ultraviolet rays which reach the Earth's surface is about 280 nm.

The main aim in the field of sun protection has thus to date actually been to ensure good protection against UVB and UVA radiation.

The wavelength region of sunlight, however, extends not only over the region of UVA and UVB radiation from 280 to 400 nm. The region perceptible to the eye extends to 800 nm and is delimited by the transition into the long-wave infrared radiation, which is perceived as thermal radiation. At the lower end, the radiation enters the short-wave UV region, also called UVC radiation. This is the wavelength region from 100 to 280 nm.

Sunlight in the wavelength region from 400 to 800 nm (VIS region) and above (IR region) can penetrate into the deeper layers of the skin and cause damage there, so that the effect of this light alone may also accelerate skin aging processes.

An object of the invention was thus to provide cosmetically well-tolerated light protection filters which also offer protection against sunlight in the wavelength region from 400 to 800 nm and in the IR wavelength region above 800 nm.

In addition, it was desirable to find an effective IR protection filter for the IR wavelength region above 800 nm which is not regarded negatively as a result of severe "whitening" on the skin, as has hitherto been the case.

An object of the invention was also to provide cosmetic formulations which offer protection against the damaging effect of sunlight both in the UV region and also in the long-wave region, the VIS and IR region. This means that formulations are to be provided which exhibit complete protection against the entire solar spectrum which reaches the Earth, as happens, for example, through clothing. The object was thus to provide cosmetically well-tolerated formulations which offer such broad-band or ultraspectral protection.

The object is achieved by light protection filters effective in the wavelength region from 400 to 800 nm (VIS region) and in the wavelength region above 800 nm (IR region), these being substances which are soluble or insoluble in cosmetic formulations or mixtures of soluble and insoluble substances.

The invention thus provides light protection filters effective in the wavelength region from 400 to 800 nm (VIS region) and in the infrared wavelength region (IR region) from 800 nm.

According to the invention, such filters may comprise pigments and/or dyes which reflect and/or absorb in the visible wavelength region (VIS reflecting). Such pigments may, in particular, be golden, red, orange-, copper- or body-colored interference pigments which resemble very closely the natural color of skin.

These interference pigments are preferably platelet-shaped or ground mica having a diameter of up to 15 $\mu$m, which is coated with $SnO_2$ and/or $TiO_2$. Interference pigments whose carrier material does not consist of mica are, however, also suitable. The coatings may be doped in various ways, such as, for example, by iron or cerium.

In a particular embodiment of these pigments, the mica has a thin coating consisting of up to 18% by weight of $SnO_2$, and a coating consisting of 50–70% by weight, preferably 54–60% by weight, of $TiO_2$ having a rutile structure.

The light protection filters may also be mica having a thin coating consisting of up to 1% by weight of $SnO_2$, and a coating consisting of 50–70% by weight, preferably 54–60% by weight, of $TiO_2$ having an anatase structure, or mica having a coating consisting of 50–70% by weight, preferably 54–60% by weight, of $TiO_2$ having a rutile or anatase structure.

Suitable substances which may also be used as VIS and/or as IR filters are pearlizing pigments consisting of mica or other carrier materials which are coated with titanium dioxides or iron oxides; in particular, these are Silver pigments (mica+$TiO_2$) having particle sizes <200 $\mu$m, in particular <15 $\mu$m, such as, for example, Timiron MP 1005® or MP 1001® available commercially, or also coarser fractions Interference pigments (mica+$TiO_2$) having particle sizes <200 $\mu$m, in particular having particle sizes of from 5 to 25 $\mu$m, with golden, red, orange-, copper- or body-colored interference, such as, for example, Timiron Silk Red® or Silk Gold® or Super Red® or Super Gold® or Super Copper® or coarser fractions or other interference colors and mixtures thereof Gold pigments (mica+$TiO_2$ and iron oxides) having particle sizes of <200 $\mu$m, in particular <5–25 $\mu$m or <15 $\mu$m; such a gold pigment is, for example, Timiron MP 20®, but coarser gold pigment fractions are also suitable Colored pigments (mica+$TiO_2$ and iron oxides) having particle sizes of <200 $\mu$m, in particular <5–25 $\mu$m or <15 $\mu$m; suitable colored pigments are, for example, Dichrona® or Microna® matt.

Also suitable are VIS-absorbing or -reflecting fillers, such as, for example, mica coated with $TiO_2$ and/or $BaSO_4$. These also include, for example, Biron® (BiOCl), Low Luster® or Extender W®, provided they are not 100% transparent.

The invention also provides mixtures of the pigments, pearlizing pigments, VIS-reflecting absorbing fillers or dyes given above and below as light protection filters according to the invention.

Normally used as UV filters, microfine ZnO and $TiO_2$ particles are also suitable as such, provided they also reflect or absorb in the VIS region. These are available commercially under the names Hombitec® or Sachotec®, Kemira M160®, Tioveil AQ® and, to a limited extent, Eusolex T-2000®, limited since it has very high transparency.

Suitable VIS filters can also be dyes approved in cosmetics, for example chosen from the "Blaue Liste" (Blue List) (list of dyes permitted in cosmetics)["Blaue Liste" (Blue List) edition Cantor Verlag, editor H. P. Fiedler (1993)], which can be used either as they are or else in a mixture. These dyes can also be used as undissolved pigments. Those which are particularly suitable here are the red, yellow and blue dyes, which individually or in a mixture with the other additives give formulations which, when applied to the skin, have a natural color. It is thus also possible to use dyes from this list having colors other than those mentioned, such as, for example, orange or gold.

Preferred red dyes are those with the names D&C Red, preferably with the numbers No. 10, C.I. 15630, No. 7, C.I. 15850 and No. 21, C.I. 45380, Acid Red, preferably Acid Red No. 1, C.I. 18050, Allura Red, trans-alpha-, beta- or gamma-carotene and Pigment Red. Yellow dyes in this respect are those with the names Acid Yellow, preferably Acid Yellow No. 1, C.I. 10316, tartrazine, C.I. 19140, rutin, D&C Yellow No. 7, C.I. 45350, Disperse Yellow, Food Yellow, Natural Yellow, Pigment Yellow and Solvent Yellow.

Suitable blue dyes are Acid Blue, preferably Acid Blue No. 9, C.I. 42090, Acid Blue No. 80, C.I. 61585, D&C Blue No. 6, C.I. 73000, C-Blue 21 and Direct Blue 86.

As well as the dyes listed in the given list, other VIS-absorbing substances are also suitable, such as, for example, flavonoids or natural or artificial melanin.

In addition, the VIS filters may, in addition to their protective effect in the VIS region, also have a protective effect in the UV or IR region.

Protection of the skin against IR radiation is also sensible and important since IR radiation in sunlight contributes significantly to warming. This heat in turn is synergistic in the development of erythema caused by UV, i.e. it promotes the development of sunburn.

In this connection, suitable IR protection filters are basically many substances described for the VIS region, in particular the interference pigments, which are effective in the longer-wave region. The transition between the VIS and the IR region is often smooth.

Pigments reflecting in the IR region are thus preferably used. However, the severe "whitening" on the skin is often considered to be in need of improvement. The object of this invention was achieved by the provision of a novel interference pigment effective in the IR wavelength region.

The invention thus also provides an interference pigment for IR protection, characterized in that the pigment has a white body color and a yellowish, copper- or skin-colored interference color.

This interference pigment consists of platelet-shaped or ground mica which is coated with $TiO_2$ of varying layer thicknesses and which in addition may also be doped with iron or cerium.

The novel interference pigments have shades in the range copper-colored, yellowish and skin-colored-pink. To describe the colors better, the shades can also be defined by codes from the "Pantone Color Formula Guide 1000", which are known to the person skilled in the art. The following shades are particularly preferred according to the invention: 726C, 489U, 489C, 712C, 155U, 719U, 1205U and also 1205C. This list is merely to be regarded as a descriptive disclosure which is in no way limiting.

Surprisingly, the novel pigments have a white body color, i.e. the formulations are white, but then on the skin, a copper- or skin-pink-colored interference color appears, as desired. There is no undesired "whitening" here.

The novel interference pigments are prepared by the generally known methods for the continuous build up of layers of $Ti(OH)_4$ on mica particles (described, for example, in documents U.S. Pat. No. 4,038,099, DE-C 25 22 572 and also EP 0 271 767 B1). The process is then stopped at the desired interference color.

The particle size is very important for the effectiveness. A very particularly preferred particle size is from 5 to 25 $\mu m$ since this permits an optimum protective effect against IR radiation to be achieved.

If the particle size is chosen to be less than about 15 $\mu m$, then this interference pigment can also be highly suitable for the VIS region.

The interference pigments for the VIS region can also be prepared, for example, by the processes described in the cited documents.

According to the invention, the VIS and IR light protection filters can in each case be used separately or, of course, also in combination, which is preferable, in cosmetic formulations such as sun-screens, skin creams, skin gels, hair gels or cosmetic sticks. In this respect, they may be used in combination either with inorganic or else with organic UVA and UVB filters or mixtures thereof.

The novel filters for protection against VIS and IR radiation can in each case be incorporated into cosmetic formulations in concentrations from 0.5 to 20% by weight, preferably from 3 to 10% by weight. In this way, it is possible to prepare formulations in which up to 100% of the light protection filters used are novel VIS and/or IR filters. These are substances which are easily dissolved in, dispersed in or emulsified with water and oils.

The novel light protection filters can be incorporated directly into cosmetic formulations without further preparative measures.

These substances also offer the great advantage that they do not exhibit any toxic or allergic reactions towards the skin.

These cosmetic formulations exhibit significantly improved protection against the damaging effects of solar rays.

Since recent trends have been towards providing protection against UVB, UVA and also against VIS or IR radiation, i.e. achieving complete protection against the entire solar spectrum which reaches the Earth, as happens, for example, through clothing, the object of the invention was also to provide cosmetically well-tolerated formulations which offer such broad-band or ultraspectral protection.

The object is achieved by the combination of organic and/or inorganic UV filters, VIS and IR filters.

According to the invention, cosmetic formulations are thus provided which comprise light protection filters effective in the wavelength region from 280 to 400 nm (UV filters), in the wavelength region from 400 to 800 nm (VIS filters) and in the longer-wave region above 800 nm (IR filters), and thus offer hyper-protection against the sun.

A method for protecting the skin against solar rays, which comprises applying a novel cosmetic preparation to the skin, is likewise provided by the invention.

The novel formulations can either exclusively comprise inorganic light protection filters or else combinations of organic and inorganic light protection filters.

The content of UV, VIS and IR filters in the cosmetic formulations can in each case be between 0.5 and 20% by weight, preferably between 3 and 10% by weight.

The VIS and/or IR filters used are preferably the novel light protection filters described in detail in this document.

Suitable UV filters are inorganic and organic light protection filters. Inorganic UV filters which may be used are UV filters generally known to the person skilled in the art, such as, for example, those from the group consisting of titanium dioxide and zinc oxide. Available commercially is also, for example, Eusolex® T-2000 (Merck KGaA, Darmstadt), a micronized titanium dioxide.

These inorganic UV filters are usually incorporated into cosmetic formulations in an amount of from 0.5 to 20% by weight, preferably 2–10%.

Suitable organic UV filters are all UVA and UVB filters known to the person skilled in the art. For both UV ranges, there are many tried and tested substances known from specialist literature, it being possible to list here, for example, only substances such as benzylidenecamphor derivatives (e.g. Eusolex® 6300) or phenylbenzimidazole-5-sulfonic acid (Eusolex® 232), benzoyl- or dibenzoylmethane such as Eusolex® 9020 or Eusolex® 8020, benzophenones (Eusolex® 4360), methoxycinnamate (e.g. Eusolex® 2292), salicylate derivatives (e.g. Eusolex® OS), octocrylene (Eusolex® OCR), 4-amino-benzoic acid (PABA), homosalicylate (HMS) and also octyltriazone (Uvinol® T 150).

These organic UV filters are usually incorporated into cosmetic formulations in an amount of from 0.5 to 10% by weight, preferably 1–8% by weight, particularly preferably from 3 to 6% by weight.

The various light protection filters can be directly combined in all possible variants and incorporated into cosmetic formulations.

Preferred embodiments of the invention comprise, for example, the following combinations: pigments for VIS protection (3–5% by weight), IR filters (3–5% by weight) and organic UV filters (5–10% by weight); VIS filters (3–5% by weight), IR filters (3–5% by weight) and inorganic and organic UV filters (5–20% by weight).

These are substances which can be easily dissolved in, dispersed in or emulsified with water and oils. They disperse uniformly in traditional cosmetic carriers and are able, particularly in fatty carriers, to form a continuous film. In this manner, they can be applied to the skin in order to form an effective protective film.

The novel formulations have total protection against solar irradiation and also a lasting protective effect.

The novel VIS and IR filters exhibit high chemical stability, i.e. they do not undergo hydrolysis, photooxidation or oxidation, have high thermal stability and high resistance to sweat.

The novel VIS and IR filters can be used to prepare cosmetic preparations which have a protective action and absorb radiation in a significantly broader wavelength range.

If desired, the novel sunscreens may also comprise one or more chemical substances having self-tanning properties.

Chemical substances having self-tanning properties which may be used are all natural and synthetic substances known to the person skilled in the art which are suitable for the preparation of cosmetic formulations. These may either be vegetable extracts or synthetic self-tanners such as, for example, dihydroxy-acetone or $\alpha$-ketols.

The novel formulations have total protection against solar irradiation and also a lasting protective effect.

The invention relates to light protection in the visible wavelength region from 400–800 nm (VIS protection).

In addition to their protective effect in the VIS region, the VIS filters may also have a protective effect in the UV or IR region.

In addition, the novel interference pigments having a white body color for IR protection may also have a protective effect in the VIS region.

Furthermore, the novel formulations may also be used for the preventive treatment of inflammation and allergies of the skin and also in certain cases for preventing certain types of cancer.

The novel preparation is used as a product for protecting the human epidermis or hair or also sensitized hair or as a sunscreen.

"Sensitized hair" is taken to mean hair which has been subjected to a permanent wave treatment or to a dyeing or bleaching process.

A method for protecting the hair against solar irradiation which comprises applying a novel cosmetic preparation to the hair is also provided by the invention.

The novel cosmetic preparation is used for protecting the human epidermis against solar irradiation. For this purpose, it is in various forms customarily used for this type. For example, it can, in particular, be in the form of a lotion or emulsion, such as a cream or milk (O/W, W/O), or in the form of oily or oily-alcoholic lotions, emulsions, such as creams or as milk, in the form of oily-alcoholic, oily-aqueous or aqueous-alcoholic gels or as solid sticks, or be formulated as an aerosol.

The formulation may comprise cosmetic adjuvants which are customarily used in this type of preparation, such as, for example, thickeners, emollients, moisturizers, surfactants, emulsifiers, preservatives, antifoams, perfumes, waxes, lanolin, propellants, dyes and/or pigments which color the product itself or the skin, and other ingredients customarily used in cosmetics.

The dispersant or solubilizer used may be an oil, wax or other fatty substance, a low molecular weight monoalcohol or a low molecular weight polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and, firstly, in addition to one or more light protection filters, includes at least one VIS and/or IR filter, and, secondly, in the case of a preparation for ultraspectral protection, in addition to the novel combination of light protection filters, includes fatty alcohols, fatty acids, fatty acid esters, in particular triglycerides of fatty acids, lanolin, natural or synthetic oils or waxes and emulsifiers in the presence of water.

Other preferred embodiments are oily lotions based on natural or synthetic oils and waxes, lanolin, fatty acid esters, in particular triglycerides of fatty acids, or oily-alcoholic lotions based on a low molecular weight alcohol, such as ethanol, or a glycol, such as propylene glycol, and/or a polyol, such as glycerol, and oils, waxes and fatty acid esters, such as triglycerides of fatty acids.

The novel cosmetic preparation may also be in the form of an alcoholic gel which comprises one or more low molecular weight alcohols or polyols, such as ethanol, propylene glycol or glycerol, and a thickener, such as diatomaceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

The invention also provides cosmetic sunscreens which comprise at least the novel combination of UV, VIS and IR filters for achieving hyperprotection against the sun.

The invention also provides cosmetic sunscreens which comprise at least one or more of the described VIS light protection filters. The invention also provides cosmetic sunscreens which comprise at least one of the described IR filters or at least one of the novel interference pigments having a white body color for IR protection.

If a preparation is formulated as an aerosol, the customary propellants, such as alkanes, fluoroalkanes and chlorofluoroalkanes, are normally used.

If the novel product is to protect natural or sensitized hair against solar irradiation, it can be in the form of a shampoo, lotion, gel or emulsion for rinsing out, the respective formulation being applied before or after shampooing, before or after dyeing or bleaching or before or after permanent waving; or the product is in the form of a lotion or gel for styling and treating, a lotion or gel for brushing or setting a water-wave, a hairspray, permanent wave solution, dye or bleach for the hair. Apart from the novel light protection filters (VIS and/or IR filters) or the novel combination of light protection filters, this product may comprise a variety of adjuvants used in this type of product, such as surfactants, thickeners, polymers, emollients, preservatives, foam stabilizers, electrolytes, organic solvents, silicone derivatives, oils, waxes, degreasing agents, dyes and/or pigments which color the product itself or the hair or other ingredients customarily used for hair care.

The novel cosmetic preparations may be prepared using techniques well known to the person skilled in the art.

The entire disclosure of all applications, patents and publications, cited above and below, and of corresponding German applications 197 34 582.4, filed Aug. 9, 1997; 197 46 139.5, filed Oct. 8, 1997; and 197 50 028.5, filed Nov. 12, 1997, are hereby incorporated by reference.

The following examples serve to illustrate the invention in more detail. All percentages are by weight.

EXAMPLE 1

The following components are used to prepare a novel sunscreen comprising VIS light protection filters.

|   |   |   | % by weight |
|---|---|---|---|
| A | Eusolex ® 9020 (Art. No. 105844) | (1) | 1.00 |
|   | Eusolex ® OCR (Art. No. 105377) | (1) | 3.00 |
|   | Arlatone 983 S | (2) | 1.50 |
|   | Arlatone 985 | (2) | 2.20 |
|   | Brij 76 | (2) | 1.50 |
|   | Miglyol 812 neutral oil | (3) | 9.50 |
| B | Eusolex ® VIS | (1) | 5.00 |
|   | Sorbitol F liquid (Art. No. 102993) | (1) | 2.50 |
|   | 1,2-Propanediol (Art. No. 107478) | (1) | 2.50 |
|   | Preservative |  | q.s. |
|   | Demin. Water |  | ad 100.00 |
| C | Carbomer 934 | (4) | 0.50 |
| D | Tris (hydroxymethyl) aminomethane (Art. No. 108386) | (1) | 0.36 |
|   | Demin. Water |  | 9.64 |

Phase B is prepared by thoroughly mixing together all of the components. C is then added and mixed in by stirring. The resulting mixture is left undisturbed to swell until a homogeneous mixture has been formed. Meanwhile, Phase D is prepared by mixing tris(hydroxymethyl)aminomethane with the stated amount of water. D is added to the previously prepared mixture B-C and stirred until a homogeneous phase has formed. The resulting phase B-D is heated to 80° C. At the same time, all components of phase A are mixed together and heated to 75° C. The heated phase B-D is slowly mixed with stirring with the heated phase A. The mixture is then allowed to cool.

Possible preservatives are:

0.05% of propyl 4-hydroxybenzoate (Art. No. 107427) or 0.15% of methyl 4-hydroxybenzoate (Art. No. 106757).

Sources of supply:

(1) Merck KGaA, Darmstadt (2) ICI, Essen (3) Hüls Troisdorf AG, Witten (4) Goodrich, Neuss

Example 2

The following components are used to prepare a novel sunscreen cream (O/W) having ultraspectral protection comprising inorganic light protection filters.

|   |   |   | % by weight |
|---|---|---|---|
| A | Arlatone 983 S | (2) | 1.50 |
|   | Arlatone 985 | (2) | 2.20 |
|   | Brij 76 | (2) | 1.50 |
|   | Miglyol 812 neutral oil | (3) | 9.50 |
| B | Eusolex ® T-2000 (Art. No. 105373) | (1) | 5.00 |
|   | Eusolex ® VIS | (1) | 5.00 |
|   | Timiron Silk Gold ® (Art. No. 117239) | (1) | 2.50 |
|   | Timiron Silk Red ® (Art. No. 117240) | (1) | 2.50 |
|   | Sorbitol F liquid (Art. No. 102993) | (1) | 2.50 |
|   | 1,2-Propanediol (Art. No. 107478) | (1) | 2.50 |
|   | Preservative |  | q.s. |
|   | Demin. Water |  | ad 100.00 |
| C | Carbomer 934 | (4) | 0.50 |
| D | Tris (hydroxymethyl) aminomethane (Art. No. 108386) | (1) | 0.36 |
|   | Demin. water |  | 9.64 |

Possible preservatives are:

0.05% of propyl 4-hydroxybenzoate (Art. No. 107427) or 0.15% of methyl 4-hydroxybenzoate (Art. No. 106757).

Preparation:

Carbomer 934 is added to the combined phase B and the mixture is left to swell until it is homogeneous. Phase D, which has been pre-dissolved, is then added and the mixture is stirred until the phases are mixed homogeneously. This mixture is then heated to 80° C., and phase A is also mixed and heated to 75° C. The mixture B-D is then introduced into phase A with stirring, and the mixture is carefully stirred until cool.

Sources of supply:

(1) Merck KGaA, Darmstadt (2) ICI, Essen (3) Hüls Troisdorf AG, Witten (4) Goodrich, Neuss

Example 3

The following components are used to prepare a novel sunscreen cream (O/W) with ultraspectral protection comprising inorganic and organic light protection filters.

|   |   | % by weight |
|---|---|---|
| A Eusolex ® 9020 (Art. No. 105844) | (1) | 1.00 |
| Eusolex ® 2292 (Art. No. 105382) | (1) | 3.00 |
| Eusolex ® 6300 (Art. No. 5385) | (1) | 1.00 |
| Arlatone 983 S | (2) | 1.50 |
| Arlatone 985 | (2) | 2.20 |
| Brij 76 | (2) | 1.50 |
| Miglyol 812 neutral oil | (3) | 9.50 |
| B Eusolex ® VIS | (1) | 5.00 |
| Timiron Silk Gold ® (Art. No. 117239) | (1) | 2.50 |
| Timiron Silk Red ® (Art. No. 117240) | (1) | 2.50 |
| Sorbitol F liquid (Art. No. 102993) | (1) | 2.50 |
| 1,2-Propanediol (Art. No. 107478) | (1) | 2.50 |
| Preservative |   | q.s. |
| Demin. water |   | ad 100.00 |
| C Carbomer 934 | (4) | 0.50 |
| D Tris (hydroxymethyl) aminomethane (Art. No. 108386) | (1) | 0.36 |
| Demin. water |   | 9.64 |

Possible preservatives are:

0.05% of propyl 4-hydroxybenzoate (Art. No. 107427) or 0.15% of methyl 4-hydroxybenzoate (Art. No. 106757).

Preparation:

Carbomer 934 is added to the combined phase B and the mixture is left to swell until it is homogeneous. Phase D, which has been pre-dissolved, is then added and the mixture is stirred until the phases are mixed homogeneously. This mixture is then heated to 80° C., and phase A is also mixed and heated to 75° C. The mixture B-D is then introduced into phase A with stirring, and the mixture is carefully stirred until cool.

Sources of supply:

(1) Merck KGaA, Darmstadt (2) ICI, Essen (3) Hüls Troisdorf AG, Witten (4) Goodrich, Neuss Example 4

The following components are used to prepare a novel sunscreen cream (W/O) having UVA/B and IR protection.

|   |   | % by weight |
|---|---|---|
| A Eusolex ® 9020 (Art. No. 105844) | (1) | 5.00 |
| Eusolex ® 2292 (Art. No. 105382) | (1) | 2.00 |
| Abil EM 90 | (2) | 2.50 |
| Jojoba oil | (3) | 8.00 |
| Cetiol V | (4) | 8.00 |
| Prisorine 2021 | (5) | 4.50 |
| Castor oil | (6) | 0.80 |
| Lunacera W 80 | (7) | 1.20 |
| B Eusolex IR | (1) | 5.00 |
| Glycerol (Art. No. 4093) | (1) | 2.00 |
| Sodium chloride (Art. No. 6400) | (1) | 0.40 |
| Preservative |   | q.s. |
| Demin. water |   | ad 100.00 |

Possible preservatives are:

0.05% of propyl 4-hydroxybenzoate (Art. No. 107427) or 0.15% of methyl 4-hydroxybenzoate (Art. No. 106757).

Preparation:

The components of phase A are mixed and heated to 75° C. Phase B, which has been premixed, is introduced into this phase with stirring. The mixture is stirred until a homogeneous mixture is obtained, which is left to cool with stirring. If desired, fragrances may be added.

Sources of supply:

(1) Merck KGaA, Darmstadt (2) Th. Goldschmidt, Essen (3) Lamotte, Bremen (4) Henkel KGaA, Düsseldorf (5) Unichema, Emmerich (6) Heess, Stuttgart (7) Fuller, Lüneburg

EXAMPLE 5

The following components are used to prepare a novel sunscreen lotion (O/W) with UV and IR protection.

|   |   | % by weight |
|---|---|---|
| A Eusolex ® 6300 (Art. No. 105385) | (1) | 2.00 |
| Eusolex ® 2292 (Art. No. 105382) | (1) | 0.50 |
| Amphisol | (2) | 4.00 |
| Cetyl alcohol (Art. No. 100989) | (1) | 1.00 |
| Stearic acid (Art. No. 100671) | (1) | 3.00 |
| Cetiol OE | (3) | 3.00 |
| Dow Corning 200 (100 cs) | (4) | 1.00 |
| Eutanol G | (3) | 2.00 |
| Cetiol SN | (3) | 2.00 |
| Shea butter | (5) | 2.00 |
| Cetiol J 600 | (3) | 2.00 |
| Antaron V 220 | (6) | 1.00 |
| B Eusolex IR | (1) | 5.00 |
| 1,2-Propanediol (Art. No. 107478) | (1) | 2.50 |
| Sorbitol F liquid (Art. No. 102993) | (1) | 2.50 |
| Carbomer Ultrez 10 | (7) | 0.025 |
| Preservative |   | q.s. |
| Demin. Water |   | ad 100.00 |
| C Tris (hydroxymethyl) aminomethane (Art. No. 108386) | (1) | 0.025 |
| Demin. water |   | 5.00 |

Possible preservatives are:

0.05% of propyl 4-hydroxybenzoate (Art. No. 107427) or 0.15% of methyl 4-hydroxybenzoate (Art. No. 106757).

Preparation:

Firstly, phase B is prepared by firstly dispersing the carbomer in the water and then adding the other components. Phase C is added to phase B. The components of phase A are mixed and heated to 75° C. This heated phase is then slowly added to phase B/C and homogenized with stirring.

Sources of supply:

(1) Merck KGaA, Darmstadt (2) Givaudan-Rours, Geneva (3) Henkel KGaA, Düsseldorf (4) Dow Corning, Düsseldorf (5) Wagner, Bremen (6) ISP, Frechen (7) Goodrich, Neuss

EXAMPLE 6

The following components are used to prepare a novel sunscreen cream (O/W) having UVA/B and IR protections.

|   |   | % by weight |
|---|---|---|
| A | Eusolex ® 6300 (Art. No. 105385) (1) | 3.00 |
|   | Eusolex ® 4360 (Art. No. 105376) (1) | 2.00 |
|   | Arlacel 165 V (2) | 10.00 |
|   | Cetyl alcohol (Art. No. 100989) (1) | 3.00 |
|   | Eutanol G (3) | 5.00 |
|   | Cetiol OE (3) | 5.00 |
|   | Cetiol B (3) | 5.00 |
|   | Dow Corning (4) | 2.00 |
| B | Eusolex IR (1) | 5.00 |
|   | Eusolex 232 (Art. No. 105372) (1) | 2.00 |
|   | Tris (hydroxymethyl) aminomethane (Art. No. 108386) (1) | 0.90 |
|   | Sorbitol F liquid (Art. No. 2993) (1) | 3.00 |
|   | Glycerol (Art. No. 4093) (1) | 2.00 |
|   | Titriplex III (Art. No. 8421) (1) | 0.05 |
|   | Preservative | q.s. |
|   | Demin. water | ad 100.00 |

Possible preservatives are:
0.05% of propyl 4-hydroxybenzoate (Art. No. 107427) or
0.15% of methyl 4-hydroxybenzoate (Art. No. 106757).
Preparation:

Phase B is prepared by firstly dissolving tris (hydroxymethyl)aminomethane in the water and adding Eusolex 232 with stirring. The other ingredients are then added and the mixture is heated to 80° C. The components of phase A are mixed and heated to 75° C. Phase B is then slowly added to phase A with careful stirring, and the mixture is stirred until homogeneous. The mixture is then left to cool with stirring and at 40° C. it is possible to add perfume substances, if desired.

Sources of supply:
(1) Merck KGaA, Darmstadt
(2) ICI, Essen
(3) Henkel KGaA, Düsseldorf
(4) Dow Corning, Düsseldorf The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An interference pigment material, comprising at least one of
   (a) a copper and/or skin-colored interference pigment which is platelet-shaped or ground mica having a diameter of up to 15 μm, which is coated with $SnO_2$ and/or $TiO_2$, said coating being optionally doped with iron or cerium; or
   (b) an interference pigment having a white body color and a copper or skin-colored interference color and is platelet-shaped or ground mica, which is coated with $TiO_2$ and optionally doped with iron or cerium and has a particle size of less than 15 μm.

2. An interference pigment material according to claim 1, wherein the interference pigment material absorbs or reflects radiation in the wavelength region from 400 to 800 nm or in the wavelength region from 800 nm, or both.

3. An interference pigment material according to claim 2, wherein the interference pigment material is soluble in cosmetic formulations.

4. A light protection filter composition comprising an interference pigment material according to claim 1 and at least one dye, wherein the dye is soluble or insoluble in cosmetic formulations, and wherein the dye reflects or absorbs visible or IR radiation.

5. An interference pigment material according to claim 1, wherein the material is
   (a) a copper or skin-colored interference pigment which is platelet-shaped or ground mica having a diameter of up to 15 μm, and which is coated with $SnO_2$ and/or $TiO_2$, said coating optionally doped with iron or cerium.

6. An interference pigment material according to claim 1, wherein the material is
   (b) an interference pigment having a white body color and a copper or skin-colored interference color and is platelet shaped or ground mica, which is coated with TiO2 and optionally doped with iron or cerium and has a particle size of less than 15 μm.

7. An interference pigment material according to claim 1, wherein the material is mica having a $TiO_2$ coating, wherein the $TiO_2$ coating comprises 50% to 70% by weight of the coated mica, and wherein the mica optionally has a thin coating of $SnO_2$ comprising up to 1% by weight of the coated mica.

8. A cosmetic formulation, sunscreen, skin cream, skin gel, hair gel or cosmetic stick comprising an interference pigment material according to claim 1.

9. A composition according to claim 8, further comprising inorganic and/or organic UVA and/or UVB filters.

10. A composition according to claim 8, having a content of UV, VIS and IR filters, each from 0.5 to 20% by weight.

11. A composition according to claim 9, wherein the inorganic UV filters used are titanium dioxide or zinc oxide.

12. A composition according to claim 9, wherein organic UV filters are used and are benzoyl- or dibenzoylmethane compounds, a methoxycinnamate, a salicylate compound, a benzylidenecamphor compound, octocrylene, a benzophenone, phenylbenzimidazole-5-sulfonic acid, 4-aminobenzoic acid, octyltriazone or octyldimethyl PABA.

13. A method of blocking visible and/or IR radiation from the skin of a host comprising applying an effective amount of an interference pigment material according to claim 1 to the skin of the host.

14. A method according to claim 13, wherein visible and IR radiation are simultaneously blocked.

15. A method of blocking visible and/or IR radiation from the skin of a host comprising administering an effective amount of a composition according to claim 9.

16. A method according to claim 13, wherein the host is a male human, an infant, a child, or a female under 12 years of age.

17. A sunscreen or cosmetic composition comprising an interference pigment material according to claim 1, wherein the composition has been formulated to increase its visible radiation blocking character.

18. A sunscreen or cosmetic composition comprising an interference pigment material according to claim 1, wherein the composition has been formulated to increase its visible radiation blocking character.

19. A sunscreen or cosmetic composition comprising an interference pigment material according to claim 1, wherein the material is mica having a $TiO_2$ coating, wherein the $TiO_2$ coating comprises 50% to 70% by weight of the coated mica, and wherein the mica optionally has a thin coating of $SnO_2$ comprising up to 1% by weight of the coated mica, wherein the composition has been formulated to increase its visible radiation blocking character.

20. A sunscreen or cosmetic composition comprising an interference pigment material according to claim 1, wherein the material is mica having a $TiO_2$ coating, wherein the $TiO_2$ coating comprises 50% to 70% by weight of the coated mica, and wherein the mica optionally has a thin coating of $SnO_2$ comprising up to 1% by weight of the coated mica, wherein the composition has been formulated to increase its visible radiation blocking character.

21. An interference pigment material comprising at least one of
 (a) a copper and/or skin-colored interference pigment comprising particles, wherein the particles comprise a carrier material coated with SnO2 and/or $TiO_2$, said coating being optionally doped with iron or cerium, wherein the particles have a size of less than 15 µm; or
 (b) an interference pigment having a white body color and a copper or skin-colored interference color, wherein the interference pigment comprises particles, wherein the particles comprise a carrier material coated with $TiO_2$ and optionally doped with iron or cerium, wherein the particles have a size of less than 15 µm.

22. An interference pigment material, comprising at least one of
 (a) a copper and/or skin-colored interference pigment which is mica having a diameter of up to 15 µm, which is coated with $SnO_2$ and/or $TiO_2$, said coating being optionally doped with iron or cerium; or
 (b) an interference pigment having a white body color and a copper or skin-colored interference color and is mica, which is coated with $TiO_2$ and optionally doped with iron or cerium and has a particle size of less than 15 µm.

* * * * *